(12) United States Patent
Benjamin

(10) Patent No.: US 8,283,180 B2
(45) Date of Patent: Oct. 9, 2012

(54) PERIODIC ACID-SCHIFF STAINING WITH DETECTION IN THE INFRARED RANGE

(75) Inventor: Elfrida Benjamin, Millstone, NJ (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 238 days.

(21) Appl. No.: 12/595,760

(22) PCT Filed: Apr. 11, 2008

(86) PCT No.: PCT/US2008/060104
§ 371 (c)(1),
(2), (4) Date: Mar. 19, 2010

(87) PCT Pub. No.: WO2008/128098
PCT Pub. Date: Oct. 23, 2008

(65) Prior Publication Data
US 2010/0178667 A1    Jul. 15, 2010

Related U.S. Application Data

(60) Provisional application No. 60/911,688, filed on Apr. 13, 2007.

(51) Int. Cl.
*G01N 21/76*     (2006.01)
*G01N 33/533*    (2006.01)

(52) U.S. Cl. .................. 436/172; 436/546; 436/800

(58) Field of Classification Search .................. None
See application file for complete search history.

(56) References Cited

U.S. PATENT DOCUMENTS
2004/0204379 A1   10/2004   Cheng et al.

FOREIGN PATENT DOCUMENTS
GB    2206691 A    1/1989
WO    WO 2006/125141 A2    11/2006

OTHER PUBLICATIONS

Nettleton et al. Studies of the mechanism of the periodic acid-schiff histochemical reaction for glycogen using infrared spectroscopy and model chemical compounds. Stain Technology 1977, vol. 52, No. 2, pp. 63-77.*
Changaris et al. A microfluorescent PAS method for the quantitative demonstration of cytoplasmic 1,2-glycols. Histochemistry 1977, vol. 52, pp. 1-15.*
Burns et al., "Staining of Blood Cells with Periodic Acid/Salicyloyl Hydrazide (PA-SH). A Fluorescent Method for Demonstrating Glycogen", Blood, vol. 28, No. 5, Nov. 1966, pp. 674-682.
Supplementary European Search Report for EP 08 74 5665, dated Sep. 10, 2010.
Changaris et al., "A microfluorescent PAS method for the quantitative demonstration of cytoplasmic 1,2-glycols", Histochemistry and Cell Biology, vol. 52, No. 1, pp. 1-15, (Mar. 1977), abstract only.
Mizuno et al., "Near-infrared Fourier transform Raman spectroscopic study of human brain tissues and tumours", Journal of Raman Spectroscopy, vol. 25, Issue 1, pp. 25-29, (1993), abstract only.
Nettleton et al., "Studies of the Mechanism of the Periodic Acid-Schiff Histochemical Reaction for Glycogen Using Infrared Spectroscopy and Model Chemical Compounds", Biotechnic and Histochemistry, vol. 52, Issue 2, pp. 63-77, (Mar. 1977), abstract only.
Schaart et al., "A modified PAS stain combined with immunofluorescence for quantitative analyses of glycogen in muscle sections", Histochem Cell Biol, vol. 122, pp. 161-169, (Aug. 2004).
International Search Report for PCT/US08/60104 mailed on Jul. 15, 2008.
Written Opinion of the International Searching Authority for PCT/US08/60104 mailed on Jul. 15, 2008.

* cited by examiner

*Primary Examiner* — Shafiqul Haq
(74) *Attorney, Agent, or Firm* — Hoffmann & Baron, LLP

(57) ABSTRACT

Provided is a method of detecting the presence and quantitating the amount of glycogen from a biological sample. This method employs PAS staining with detection in the infrared range.

11 Claims, 3 Drawing Sheets

Figure 3
A.
B.
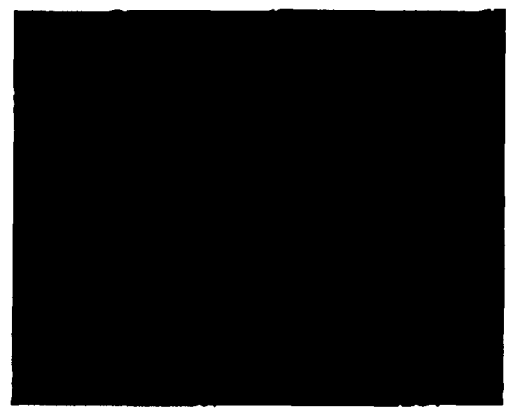
CRL-2076
PM-12

PERIODIC ACID-SCHIFF STAINING WITH DETECTION IN THE INFRARED RANGE

CROSS-REFERENCE TO RELATED APPLICATIONS

This application is the National Stage of International Application No. PCT/US2008/060104, filed Apr. 11, 2008, which claims the benefit of U.S. Provisional Application Ser. No. 60/911,688, filed Apr. 13, 2007, the entire contents of both of which are incorporated by reference herein.

FIELD OF THE INVENTION

The present invention relates to a novel method for quantifying glycogen and other polysaccharides in biological samples using a fluorescent Periodic acid-Schiff (PAS) reaction with detection in the infrared range.

BACKGROUND OF THE INVENTION

Polysaccharides are complex carbohydrates comprised of polymers made up of many monosaccharides joined together by glycosidic linkages. Polysaccharides include storage polysaccharides such as starches and glycogen, and structural polysaccharides such as cellulose, acid polysaccharides containing sialic acid or sulfuric ester groups, and chitin. Polysaccharides have diverse biological functions including long term storage of sugars (for energy), and structural support and protection to organisms; cellulose is a major component of cell walls in plants and bacteria, and chitin is a component of fungi cell walls and exoskeletons of arthropods. Polysaccharides are also involved in molecular recognition (antigens) by cells of the immune system.

Glycogen is a storage polysaccharide comprised of glucose. Most of the glucose units are linked by $\alpha$-1,4 glycosidic bonds, but approximately 1 in 12 glucose residues also makes $\alpha$-1,6 glycosidic bond with a second glucose, which results in the creation of a branch. Glycogen is present in a wide variety of tissues, including skin, liver, parathyroid glands and skeletal and cardiac muscle. Detection of glycogen is used in clinical settings for the diagnosis of diseases including cancer, infections (fungus, *Chlamydia*), diabetes (Type 1), myopathies, glycogen storage disease (Pompe disease), and other glycogenoses. Histochemical detection of glycogen also is used to identify structures such as connective tissues, mucus, and basal laminae, corporal amylacea, polygucosan bodies and other substances in biological samples, all of which contain a high proportion of carbohydrate macromolecules (glycogen, glycoprotein, proteoglycans). Specifically, PAS is used to stain neutral mucopolysaccharides, such as those in glands of the GI tract and in prostate; simple acidic polysaccharides containing sialic acid, such as those found in epithelial cells; and complex sulfated acid polysaccharides such as those found in adenocarcinomas.

Historically, imaging of polysaccharide, e.g., glycogen, content in cells and tissues has been measured qualitatively using the Periodic acid-Schiff (PAS) reaction. PAS stains glycogen and other polysaccharide molecules based on periodic acid-induced oxidative cleavage of carbon-to-carbon bonds in 1,2 glycols to form dialdehydes that react with fuchsin-sulphurous acid in the Schiff's reagent (pararosanilin and sodium metabisulfate) to yield a magenta-like stain (Bancroft and Stevens, *Theory and practice of histological techniques*. Churchill Livingstone, Edinburgh, p. 436, 1977). More recently, the PAS technique has been combined with optical density measurements, and compared to optical densities of external standards with known concentrations of glycogen, to convert to quantitative glycogen values (Schaart et al., *Histochem Cell Biol*. 2004; 122:161-169).

Fluorescence intensity measurement is another approach used commonly to quantify relative or absolute amounts of select biological materials. Fluorescence occurs where a molecule in an excited state (i.e., excited by absorption of EM radiation) emits light as it falls back to the lower energy state. The emission typically is at a longer wavelength than the wavelength of the excitatory radiation absorbed, and is in the visible range of the electromagnetic spectrum. Quantitation of fluorescence intensity is straightforward, can be readily achieved with instruments ranging from microtiter plate readers, fluorescence scanners, fluorescence and confocal microscopes. The microtiter plate reader or fluorescence scanner format is particularly suitable for simultaneous quantification and comparison of a large number of samples, such as is necessary in high-throughput applications.

Near-infrared fluorescence is a technique useful for in vivo imaging, e.g., for detecting tumors. This method is based on the fact that living tissue transmits fluorescence with wavelengths in the near-IR (about 700 nm) more efficiently than it transmits light with wavelengths in the visible range, due to increased photon penetration. Both organic and inorganic fluorescence contrast agents are now available for chemical conjugation to targeting molecules for imaging. However, this technique is for in vivo detection and imaging and has not been employed to quantitate material ex vivo in biological samples.

Autofluorescence of PAS stain in the visible red range (excitation ~540-580 nm; emission ~600-640 nm) has been described (Changaris et al., *Histochemistry*. 1977; 52:1-15; Schaart et al., supra) and used for quantitative measurement of glycogen in liver sections (Changaris et al., supra). Although useful, fluorescence measurements in the visible range are subject to high background due to auto-fluorescence of biological materials in the visible range, and poor detection of signal penetration from thick tissue sections.

One strategy used to overcome the limitations of the visible range fluorescence measurements is fluorescence imaging microscopy (Brenner et al., *J Histochem Cytochem*. 1976. 24:100-11). This method requires the assembly and integration of sophisticated equipment including a light source and appropriate filters for excitation, a microscope with sensitive optics, fine focus, an XY stage control for spatially-resolved sample imaging, emission filters, a sensitive camera for image capture, and a computer for microscope control, equipped with image collection and processing software for documentation. Focusing, XY positioning, filter configuration, image capture and collection are carried out independently for each sample and fluorophore. Image processing software is used to merge the two images from each fluorophore of a given sample to view the spatial localization of the two fluorophores simultaneously. This final merged image is a qualitative image of the spatial distribution of the fluorophore probes. Additional image quantification software, that is designed to select a region of interest and quantify fluorescence intensity within that region for each fluorophore is used to quantify the fluorescence. Thus, fluorescence is measured within areas of cells or tissues of interest, and in a region defined as background. Each fluorescence measurement is corrected for the size of the region, and then background subtracted. The exquisite spatial and focal resolution that is achieved with this methodology allows for sufficient signal to background detection in the visible range. However, this method is tedious as each sample is imaged one at a time, and the captured image is processed and quantitated one at time.

As the number of samples increase, and the number of fluorophores that are imaged per sample increase, data acquisition and processing time is proportionally increased, and throughput is proportionally decreased.

Accordingly, there remains a need in the art for an improved method to quantify polysaccharides, particularly glycogen, in biological samples.

SUMMARY OF THE INVENTION

The present invention provides a method for detecting polysaccharides in a biological sample using Periodic Acid-Schiff staining followed by quantitative detection in the IR range.

In one embodiment, detection is at a wavelength in a range from about 700 nM to 800 nM. In a specific embodiment, the detection is at a wavelength of about 800 nM.

In a further embodiment, the polysaccharide is glycogen.

In some aspects of the invention, the biological sample is derived from a human or animal.

In a specific embodiment, the biological sample is derived from a human subject having or suspected of having a glycogen storage disease including but not limited to Pompe disease (including infantile-onset Pompe disease); Cori's-Forbes' disease; Andersen's disease; Tauri's disease; McArdle's disease; Phosphorylase b Kinase deficiency (Glycogenosis type VIII); equine Glycogen Branching Deficiency; Phosphoglycerate kinase A-isoform deficiency (Glycogenosis IX); Phosphoglycerate M-mutase deficiency (Glycogenosis type X); triosephosphate isomerase (TIM) deficiency; pulmonary interstitial glycogenosis; diabetic nephropathy; and Lafora's disease (myoclonus epilepsy).

In one aspect of the present invention, the biological sample isolated is cells or tissue.

In a further aspect, the tissue is selected from the group consisting of skin, liver, kidney, heart, brain, or skeletal muscle.

The present invention further relates to quantitating the level of polysaccharides present in the biological sample by comparing the amount of emitted light with that emitted from standards of known quantities of polysaccharides.

The present invention also provides a method monitoring the efficacy of treatment in a subject being treated for a glycogen storage disease by i) detecting glycogen in a first biological sample derived from the subject prior to initiation of treatment according to the method of claim 1;

ii) detecting glycogen in a second biological sample derived from the subject following initiation of treatment according to the method of claim 1;

iii) quantitating the levels of glycogen in the two samples; and iv) comparing the level of glycogen in the first sample with the level of glycogen in the second sample, where a reduction in glycogen is indicative that the treatment is effective.

BRIEF DESCRIPTION OF THE DRAWINGS

This patent application contains at least one drawing executed in color. Copies of this patent or patent application publication with color drawing(s) will be provided by the Office upon request and payment of the necessary fee.

FIG. 3 depicts fluorescent imaging of control CRL-2076 (3A) and PM-12 (3B) with detection in the visible range.

DETAILED DESCRIPTION

Figure 1:
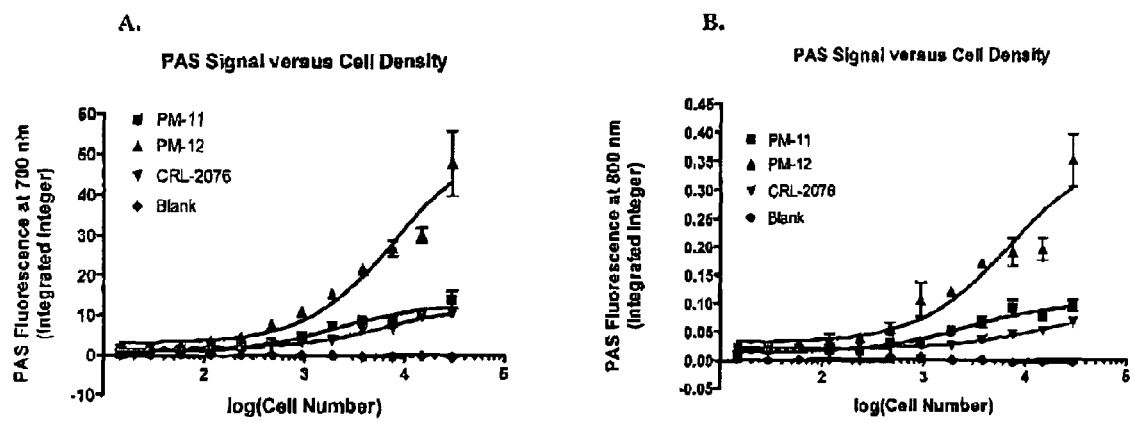
FIG. 1 depicts a concentration curve of PAS staining and detection in the near-IR range at 700 nM (1A) and 800 nM (1B) using two Pompe cells lines, one adult-onset and one infantile-onset (PM-11 and PM-12, respectively), and one normal fibroblast control.

Provided is a novel method for quantification of glycogen content from cells or tissues using PAS staining combined with IR fluorescence detection. IR fluorescence is readily quantifiable, exhibits superior signal-to-noise, superior fluorescence penetration into thick sections of tissue, and suitability for high-throughput applications. IR fluorescence detection and glycogen quantification using PAS is superior to currently available methods for quantitating glycogen content from stained cells or tissues.

To date detection of the light emissions in the IR range, has not been described for quantitating PAS-stained samples. Nettleton et al. (*Stain Technology.* 1977; 42: 63-77) describe the use of infrared absorption spectroscopy to identify the molecular composition of reaction products produced by PAS, using glycogen as a reactant. IR spectroscopy is the measurement of the wavelength and intensity of the absorption of mid-infrared light by a chemical sample. IR absorption spectroscopy is based on the ability of molecules to absorb IR radiation. This absorption of energy (photons) causes the molecules go into a higher energy state, where they vibrate or rotate. The vibrations or rotations within a molecule cause a net change in the dipole moment of the molecule, which change can be measured using infrared spectrometers. The frequencies at which there are absorptions of IR radiation ("peaks" or "signals") can be correlated directly to bonds within the compound being analyzed. Each molecule will have a unique IR spectrum.

Yano describes the use of Fourier Transform infrared (FT-IR) absorption spectroscopy for evaluation of glycogen levels in human carcinoma tissues (*Trends in Analytical Science.* 1997; 1: 1-20). However, similar to Nettleton, this is a method which depends on identification of hydrocarbons (which represent glycogen) at the molecular level using IR absorption spectroscopy.

In contrast, the present invention relates to the detection and/or quantitative measurement of glycogen levels in biological samples using IR fluorescence. Autofluorescence of biological materials is significantly lower in the infrared range (Frangioni J V., *Curr Opin Chem Biol.* 2003; 7:626-634; Ohnishi et al., *Am J Transplant.* 2006; 6:2321-31). As indicated above, fluorescence is the emission of light at a longer wavelength than the wavelength of the excitatory energy absorbed. The difference in wavelength between the peak absorbance and peak emission is the Stokes Shift. This method differs from IR absorbance spectroscopy, above, which requires that the frequency of infrared radiation passing through a molecular substance be equal to, or in resonance with, a frequency of two bonded atoms vibrating. In other words, in absorbance spectroscopy, the amount of transmitted light is measured at the same wavelength as the absorbed radiation, and the amount of transmitted light is inversely proportional to the amount of light absorbed.

The present invention demonstrates that fluorescent light detected in the IR range is superior to detection in the visible range for quantitating polysaccharide content of biological samples. This is in contrast to many fluorescent imaging systems, which contain filters for preventing the transmission of infrared light because only the visible light is desired.

Definitions

The term "infrared" covers the range of electromagnetic (EM) radiation with wavelengths of between about 700 nm-1 mm). This is in contrast to the visible red range which emits in the 600-640 nm range. In one embodiment of the present invention, the IR wavelength used to detect fluorescence is between about 700 nm and 800 nm. In another embodiment, the wavelength is about 800 nm.

"Fluorescence" is the phenomenon in which light energy ("exciting light") is absorbed by a molecule resulting in the molecule becoming "excited." After a pre-described interval, the absorbed light energy is emitted by the excited molecule. The wavelength of the emitted light is typically at a longer wavelength than the exciting light. This emitted light is referred to as fluorescent light. A molecule that exhibits fluorescence is referred to as a "fluorophore." The relationship between wavelengths of light and degree of excitation of a given fluorophore at that wavelength is described by the "excitation spectrum" of the fluorophore. The excitation spectrum is also called the excitation wavelength range. The relationship between the wavelength of light and the intensity of the fluorescence emission at that wavelength is described by the emission spectrum or fluorescence spectrum of the fluorophore. The emission spectrum is also called the emitted wavelength range. The excitation maximum is the wavelength of exciting light at which fluorescence of the fluorophore reaches maximum intensity. The emission maximum is the wavelength of light emitted by the excited fluorophore when its fluorescence is at maximum intensity.

As used herein, the terms "glycogenosis" or "glycogenoses" or "glycogen storage disease" refers to diseases or pathologies characterized by abnormal accumulation of glycogen in tissues. Such diseases or pathologies include but are not limited to the following: Pompe disease (acid maltase deficiency; Glycogenosis type II); Debrancher deficiency (Cori's-Forbes' disease; Glycogenosis type III); Branching deficiency (Glycogenosis type IV; Andersen's disease); Phosphofructokinase deficiency-M isoform (Tauri's disease; Glycogenosis type VII); Phosphorylase b Kinase deficiency (Glycogenosis type VIII); Phosphoglycerate kinase A-isoform deficiency (Glycogenosis IX); Phosphoglycerate M-mutase deficiency (Glycogenosis type X).

Other diseases which are characterized by elevated glycogen levels due to enzyme deficiencies include triosephosphate isomerase (TIM) deficiency; pulmonary interstitial glycogenosis; diabetic nephropathy; and Lafora's disease (myoclonus epilepsy).

The term "biological sample" refers to cells or tissue isolated from a human, animal, or insect, including post-mortem, which is used in an assay for diagnostic, prognostic, or histological procedures. According to the present invention, biological samples can be from any cell or tissue from a human, animal, or insect, but especially derived from the kidney, liver, brain, and skeletal muscle. In a specific embodiment, the biological sample is a tissue comprising of several cell types.

The term "subject" refers to any living eukaryotic organism including humans, animals, and insects, from which a biological sample can be obtained. In one embodiment, the subject is a mammal, particularly a human, horse, or mouse. In another embodiment, the subject is a non-mammalian animal such as a quail.

The term "effective treatment" refers to a treatment administered to a subject in need of such treatment which results in an improvement in, amelioration, or prevention of, one or more clinical symptoms, or improvement or reversal of one or more surrogate clinical markers that may be indicators of disease pathology. In one embodiment, the subject has infantile-onset Pompe disease and the surrogate clinical marker is glycogen accumulation in tissues, where a reduction in glycogen accumulation indicates that the treatment is effective.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "purified" as used herein refers to material, such as a cell, that has been isolated under conditions that reduce or eliminate unrelated materials, i.e., contaminants. For example, a purified cell is preferably substantially free of other cell types with which it is associated in a tissue. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by conventional means, e.g., chromatography, gel electrophoresis, immunoassay, composition analysis, biological assay, and other methods known in the art.

Applications

As indicated above, quantitation of glycogen and other polysaccharides in biological tissues is used for a multitude of diagnostic and prognostic purposes, and also for histological analysis of biological samples for research purposes. Some non-limiting examples are described below.

Pompe Disease.

Pompe disease (acid maltase deficiency) is caused by a deficiency in the enzyme acid α-glucosidase (GAA). GAA metabolizes glycogen, a storage form of sugar used for energy, into glucose. The accumulation of glycogen leads to progressive muscle myopathy throughout the body which affects various body tissues, particularly the heart, skeletal muscles, liver, and nervous system. According to the National Institute of Neurological Disorders and Stroke, Pompe disease is estimated to occur in about 1 in 40,000 births.

There are three recognized types of Pompe disease—infantile, juvenile, and adult onset (Hirschhorn and Reuser, In: Scriver C R, Beaudet A L, Sly W, Valle D, editors. The metabolic and molecular bases of inherited disease. Vol. III. New York: McGraw-Hill; 2001. p. 3389-420., 2001: 3389-3420). Infantile is the most severe, and presents with symptoms that include severe lack of muscle tone, weakness, enlarged liver and heart, and cardiomyopathy. Swallowing may become difficult and the tongue may protrude and become enlarged. Most children die from respiratory or cardiac complications before the age of two, although a sub-set of infantile-onset patients live longer (non-classical infantile patients). Juvenile onset Pompe disease first presents in early to late childhood and includes progressive weakness of the respiratory muscles in the trunk, diaphragm, and lower limbs, as well as exercise intolerance. Most juvenile onset Pompe patients do not live beyond the second or third decade of life. Adult onset symptoms involve generalized muscle weakness and wasting of respiratory muscles in the trunk, lower limbs, and diaphragm. Some adult patients are devoid of major symptoms or motor limitations.

Unless infantile or identified during pre-natal screening, diagnosis of Pompe disease is a challenge. Diagnosis of adult-onset Pompe is even more difficult since number, severity, and type of symptoms a patient experiences vary widely, and may suggest more common disorders such as muscular dystrophies. Diagnosis is confirmed by measuring α-glucosidase activity and/or detecting pathologic levels of glycogen from biological samples. Currently the only approved therapy is enzyme replacement therapy with recombinant α-glucosidase.

Pompe disease is one of several of glycogen pathologies. Others include Debrancher deficiency (Cori's-Forbes' disease; Glycogenosis type III); Branching deficiency (Glycogenosis type IV; Andersen's disease); Myophsophorylase (McArdle's disease, Glycogen storage disease V); Phosphofructokinase deficiency-M isoform (Tauri's disease; Glycogenosis type VII); Phosphorylase b Kinase deficiency (Glycogenosis type VIII); Phosphoglycerate kinase A-isoform deficiency (Glycogenosis IX); Phosphoglycerate M-mutase deficiency (Glycogenosis type X).

Diabetes Mellitus.

Poorly controlled diabetes mellitus results in glycogenic hepatopathy (accumulation in liver parenchymal cells) and nephropathy (glomeruli) due to the accumulation of glycogen.

Polysaccharide Storage Myopathy.

Polysaccharide storage myopathy is a neuromuscular condition found in sufferers of Glycogen Branching Enzyme Deficiency (Glycogen Storage Disease IV; Equine Rhabdomyolysis Syndrome), including American Quarter horses and related breeds. In affected horses, up to 40% of the type II muscle fibers have been found to have an acid mucopolysaccharide inclusion comprised mostly of glycogen. This results in exercise intolerance, particularly at high speeds. The abnormal accumulation typically is due to a mutation in the glycogen branching enzyme 1 (GBE1). Surgical or needle muscle biopsies which are stained by PAS or stained to detect increased ubiquitin provide a definitive diagnosis (Valentine et al., *Vet Pathol.* 2006; 43:270-275).

In humans, individuals with deficiencies in Glycogen Branching Enzyme have Andersen's disease. In most affected individuals, symptoms and findings become evident in the first months of life. Such features typically include failure to grow and gain weight at the expected rate (failure to thrive) and abnormal enlargement of the liver and spleen (hepatosplenomegaly). In such cases, the disease course is typically characterized by progressive liver (hepatic) scarring (cirrhosis) and liver failure, leading to potentially life-threatening complications.

Parasite Infections.

Many parasites, especially fungi, store food as glycogen and can thus be diagnosed using the method of the present invention. As one example filamentous fungi (dermatophytes) cause infections on the skin, nails and scalp and they constitute around 30 out of about 55 species of fungus considered to be pathogenic for man. These include *Tinea capitis, Tinea corporis, Tinea barbae, Tinea pedis* (Athlete's foot), *Tinea unguium, Blastomyces dermitiditis, Histoplasma capsulatum*, and *Cryptococcus neoformans, Sporothrix schenckii*, the yeast form of *Paracoccidioides brasiliensis*, and onychomycosis (nail fungus).

Systemic mycoses with such organisms as *Cryptococcus neoformans* and *Candida albicans* can cause life-threatening infections in humans and animals, especially in individuals who are immune suppressed. Pathogenic *Aspergillus* also poses a serious hazard for immunocompromised individuals.

Other parasites which produce glycogen are bacteria and parasitic protozoa, and include *Toxoplasma gondii* (Guimaraes et al., *Mem Inst Oswaldo Cruz.* 2003 October; 98(7):915-7); *Tropheryma whipplei* (Whipple's disease; Deriban et al., *Curr Med Chem.* 2006; 13(24):2921-6); *Entamoeba histolytica* and parasitic helminthes such as Digenean flukes, the tapeworms (Cestodes) and the roundworms (Nematodes). Whipple's disease especially is caused by a cultivation-resistant bacteria and diagnosis thus must be made by histologic analysis.

Urea Cycle Defects.

Recently, it was discovered that hepatocyte glycogen accumulation in urea cycle enzyme defects resembles that seen in glycogen storage disease. However, the accumulation in patients urea cycle enzyme defects could be distinguished in most cases by non-uniformity of distribution and/or the absence of sinusoidal compression by expanded hepatocytes (Miles et al., *J Pediatr Gastroenterol Nutr.* 2005; 40(4):471-6).

Cancer:

Elevated levels of glycogen or mucinous polysaccharides are characteristic of cancers such as chondroid lipoma, colorectal cancer and other carcinomas (e.g., brain, breast, lung, kidney). In colorectal carcinomas, it was shown using PAS staining that some of the malignant cells always produce PAS-positive mucin (Lushbaugh et al., *Digestive Diseases and Sciences.* 1985; 30: 119S-125S; U.S. Pat. No. 6,187,591). In another study, glycogen levels were shown to be highest in colorectal tumors with a high proportion of cells in G1, and decreased with progression to S phase. Takahashi et al., *J. Gastroenterology.* 1999; 34: 474-80. Glycogen-rich clear cell carcinoma of the breast also is characterized as a carcinoma in which more than 90% of the neoplastic cells have abundant clear cytoplasm that contains PAS-positive diastase-labile material, consistent with glycogen.

Histologically, chondroid lipomas are characterized by the presence of cells resembling chondroblasts and lipoblasts, mature adipose tissue, and myxoid matrix. They have irregular nuclei surrounded by clear and vacuolated cytoplasm. The vacuoles can be shown to contain lipid using the oil red O stain, and glycogen using PAS stain.

Glycogen also is found in tumors such as pancreatic islet cell tumors (Ladriere et al., *Diabetes research.* 2003; 37: 9-14; adenosquamous carcinomas of the cervix (Fujiwara et al., *Cancer.* 1995; 76:1591-1600); and in anaplastic astrocytoma, glioblastoma multiforme (Kotonski et al., *Acta Biochim Pol.* 2001; 48(4):1085-90).

Barrett's Esophagus.

Barrett's esophagus is a condition in which the esophagus, the muscular tube that carries food and saliva from the mouth to the stomach, changes so that some of its lining is replaced by a type of tissue similar to that normally found in the intestine. The risk of developing esophageal adenocarcinoma is 30 to 125 times higher in people who have Barrett's esophagus than in people who do not. Diminished or absent glycogen content is indicative of Barrett's esophagus or early esophageal squamous cell carcinoma.

Glycogenic acanthosis is another esophageal condition affecting elderly people. In glycogenic acanthosis, cytoplasmic glycogen accumulates in the squamous epithelial cell lining of the esophagus, which causes focal plaque-like thickening of the mucosa. Glycogenic acanthosis may manifest on double-contrast studies as multiple small nodules or plaques.

Progressive Mycoclonus Epilepsy.

Also known as Lafora's disease, this type of epilepsy is characterized by neuronal polyglucosan inclusions, resulting in myoclonic seizures and/or hallucinations. Polyglucosan intracellular inclusion bodies, called Lafora bodies, resemble glycogen with reduced branching, suggesting an alteration in glycogen metabolism (Fernandez-Sanchez et al., *Human Molecular Genetics*. 2003; 12: 3161-3171). The laforin protein is a phosphatase which contains a carbohydrate binding domain. Laforin interacts with another phosphatase, R5, its substrate, glycogen synthase, and intracellular glycogen to form a multiprotein complex associated with intracellular glycogen particles.

Infertility.

Decreased glycogen in endometrial biopsies can be indicative of luteal phase defect (Zawar et al., *Indian J Pathol Microbiol*. 2003; 46(4):630-3). Lutenizing hormone and follicle-stimulating hormone are glycopeptide hormones; cells containing these hormones stored in their secretory vacuoles stain positive with PAS.

Carcinogenicity.

Recent studies have shown that dichloroacetic acid (DCA), a by-product of chlorination of public water supplies, is carcinogenic to both rats and mice. Evaluation of drinking water using Japanese medaka (*Oryzias latipes*), a well characterized small fish model, is being used increasingly for carcinogenicity testing because of its low cost, ease of maintenance and carcinogen sensitivity. At low DCA exposure concentrations, changes in the liver included marked hepatocellular cytoplasmic vacuolation, cytomegaly, karyomegaly, nuclear atypia and multifocal areas of hepatocellular necrosis and loss as early as week two of DCA exposure. The majority of the hepatocellular cytoplasmic vacuoles were shown by periodic acid Schiff (PAS) staining to contain large amounts of glycogen. These elevated glycogen levels may reflect a disruption in the enzyme pathways for glycolysis.

Forensics:

Hepatic glycogen stores have long been known to decrease with starvation, trauma, acute stress, and shock, and can be evaluated using post-mortem liver biopsies. Thogmartin et al., *Am J Forensic Med Pathol*. 2001; 22(3):313-8.

In addition, alcoholic polyneuropathy is characterized by degenerating giant neurons in sympathetic ganglia which, upon autopsy, were shown to be filled with eosinophilic, periodic acid-Schiff reaction positive material.

Monitoring Contamination.

PAS has been used to detect bacterial contamination in food such as milk (Moats, *J Bacteriol*. 1959; 78(4): 589-593) and poultry; in cosmetics such as lotions (Bernd et al., *Annals of Internal Medicine*. 1996; 125; 799-806); in contact lens solutions with e.g., Acanthamoeba keratitis (Awwad et al., *Eye & Contact Lens: Science & Clinical Practice*. 2007. 33(1):1-8); and in water contamination with microorganisms (including ground water, drinking water, river and lake water).

Assays

To practice, cells (e.g., fibroblasts) are seeded onto coverslips or microtiter plates. Coverslips and microtiter plates may be tissue culture treated, or coated with fibronectin or another similar adhesion molecule. Afterward cells are fixed in 3.7% formaldehyde in PBS for 0.5 h at room temperature, then washed with deionized water for approximately 1 minute. PAS staining is then performed. Briefly, the cells are treated for about 5 minutes with 1% periodic acid, followed by washing for 1 minute in tap water, followed by a rinse in purified, deionized (e.g., milli-Q-water) water. Schiff's reagent is then applied (1% pararosanilin, 4% sodium metabisulfite, and 0.25 mol/l hydrochloric acid) and the sections incubated for about 15 minutes at room temperature. Following is another wash in milli-Q water, followed by rinsing for about 10 minutes with tap water. When using cells in a microtiter plate, the plate should be dried overnight prior to analysis. As a negative control, cells are pre-treated with diastase, which breaks down glycogen and makes it undetectable using PAS.

An approach for tissue sections entails harvest of a fresh piece of organ tissue (e.g. liver, heart, etc.) The tissue is then fixed in 3.7% formaldehyde in 90% ethanol at room temperature overnight. The tissue is then embedded in paraffin, sectioned at 5 μM thickness, then mounted onto a glass slide. Sections are deparaffinized in xylene, and re-hydrated in a graded ethanol series into a final solution of 100% water. For diastase treatment, the sections are incubated with 0.5% diastase in deionized water at room temperature for 20 minutes. The slides are then washed in deionized water. Afterward, PAS staining is then performed. Slides are immersed in 1% periodic acid for 5 min at room temperature. Slides are then rinsed several times in deionized water. Afterward, slides are immersed in Schiff's reagent for 15 min at room temperature. Slides are washed in running tap water for 5 minutes, the dried at room temperature or dehydrated through a graded ethanol series. A coverslip is then applied to the slide with xylene-based mounting media.

Fluorescence can be measured on a laser-based IR scanner, such as Odyssey®, manufactured by LiCor, Inc.

This approach can be extended to quantify absolute amounts of glycogen in cells and tissues by combining PAS staining of varying concentrations of an external glycogen standard, and quantifying the IR fluorescence emitted from the standard concentrations. A linear or non-linear regression analysis can be performed on the standard curve data, and the theoretical line or curve can be used to calculate absolute glycogen values from samples stained with PAS and measured using IR detection.

One of ordinary skill in the art will appreciate that, for high-throughput tissue screening, the procedures described herein using cells or tissues will likely need to be adapted for some tissues or for high-throughput screening. High-throughput tissue arrays on single slides has been described (Complete View™, Stratagene), and in microplates by Mat-Tek Corporation. The present invention also contemplates using the method of the present invention to detect PAS staining in solutions, including biological solution, milk, and water.

Kits

The present invention also provides for a method to develop commercial diagnostic/prognostic test kits in order to make therapeutic treatment decisions. The kit provides all materials discussed above and exemplified below for preparing and running the assay in one convenient package, including instructions and an analytic guide.

As one example, a kit will include microtiter plates, superfibronectin, diastase, periodic acid solution, Schiff's reagent, deionized water (purified), known glycogen standards, and instructions for IR detection.

EXAMPLES

Example 1

Infrared Detection of Glycogen using the PAS Reaction

PAS staining and detection in the IR using an infrared scanner at a wavelength of 800 nm was applied to cells from patients with glycogen storage disease type II (Pompe disease).

Methods

Cells.

PM-11 Pompe fibroblasts were obtained from Dr. W. J. Kleijer, Department of Cell Biology & Genetics, Erasmus University, The Netherlands. PM-12 Pompe fibroblasts were purchased from Coriell (catalog #GM03329). CRL-2076 fibroblasts (negative control) were purchased from American Type Culture Collection (Manassas, Va.). All fibroblast lines were routinely cultured at 37° C., 5% $CO_2$, in growth medium consisting of Dulbecco's Modified Minimum Essential Medium containing 15% fetal bovine serum (Hyclone, Logan, Utah), 100 U/mL penicillin; 100 µg/mL streptomycin, and 2 mM L-glutamine.

Plate Preparation.

Prior to the assay, borosilicate coverslip glass bottom 96-well black plates (Nunc; catalog #164588) are coated with superfibronectin (Sigma). Borosilicate coverslip glass bottom plates were found to have a better signal-to-background ratio (4-fold greater) than either tissue culture-treated plastic or optical-quality polymer plates (data not shown). Briefly, 100 µL of 5 µg/mL superfibronectin (Sigma) is pipetted into each well and the plate is incubated at 37° C. for 2 hours. The fibronectin solution is aspirated, the plate is washed 2 times with sterile PBS, and allowed to dry in an open-air sterile environment overnight. Plates can be stored for up to two weeks at 4° C. (wrapped in parafilm).

One day prior to the assay, cells were seeded onto the superfibronectin-coated plates. Cells were either plated at varying densities of 15,000-30,000 cells/well, or uniformly at 20,000 cells/well, and incubated overnight to permit attachment. In addition, to determine glycogen specificity of staining, one plate with cells uniformly seeded at 20,000 cells/well is treated with 0.1% diastase (α-amylase type VI-B from porcine pancreas-Sigma, catalog #A3176) and incubated for varying time-points from 5 minutes to 60 minutes (by row—5, 10, 15, 20, 30, 40, 45, and 60 minutes respectively). This also determines the incubation time that is optimal for digesting the glycogen in the sample for use as a negative control.

PAS Staining.

On the day of the assay, the plates were washed twice with PBS, and then fixed with 100 µL of 3.7% formaldehyde at room temperature for 30 minutes. Following incubation, cells were oxidized by addition of 1% periodic acid solution (Accustain, Sigma-Aldrich, catalog #395132-IL) to each well and incubated for about 5 minutes. Plates are then rinsed once in distilled water and 100 µL of Schiff's reagent is added to each well (Poly Scientific; catalog #S272), followed by a 15 minute incubation. Plates were then rinsed briefly with deionized water and then rinsed for 10 minutes under tap water to develop the reaction. Plates were then dried overnight in open air.

IR Detection.

Following the overnight incubation, the plate is read on a laser-based Odyssey IR scanner (Li-Cor, Inc.) at emission wavelengths of 700 nm (near-IR) or 800 nm (IR). The detector counts IR and near-IR fluorescence emissions independently or simultaneously from the samples, and reports these counts as arbitrary units. The detector scans across an entire microtiter plate, thus can read two fluorophores from any microtiter formatted sample array (96-well, 384-well, or other) within a few minutes. Background wells with no cells or tissue are included for background subtraction.

Results 700 nm Near-IR Detection.

Across the dynamic cell density range of about 1,000-30,000 cells/well, PM-12 fibroblasts, derived from an infantile-onset Pompe patient, exhibit significantly greater PAS fluorescence in the near-IR (700 nm; FIG. 1A) and the IR range (800 nm; FIG. 1B) than the adult-onset cell line, PM-11, or the normal control cell line CRL-2076 (about 5-fold over normal at 30,000 cells/well).

Figure 2:
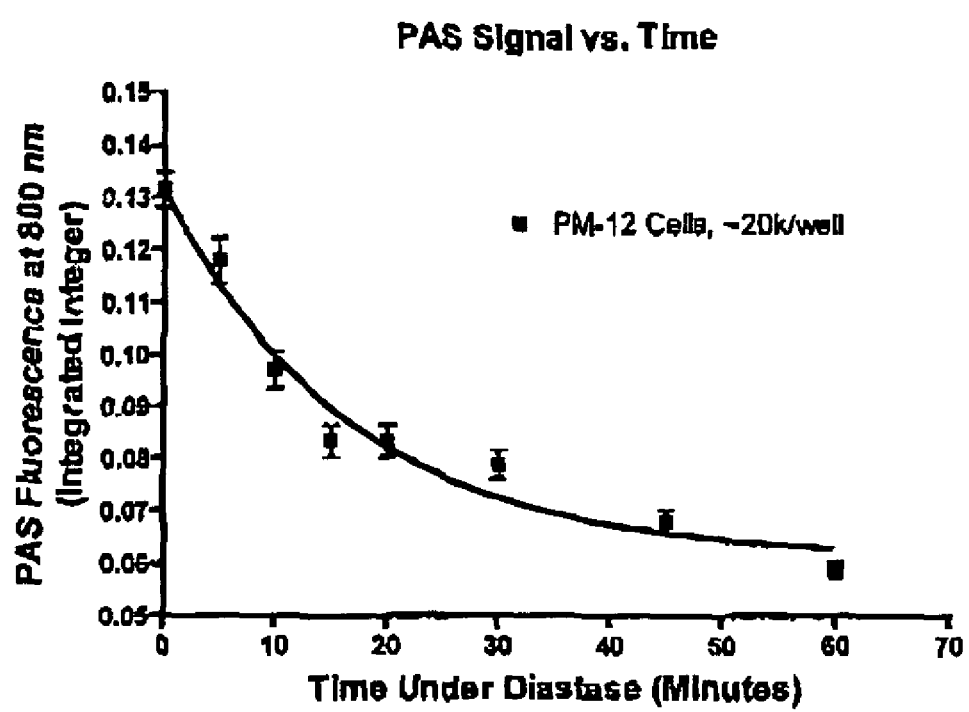
FIG. 2 depicts PAS staining of PM-12 cells with detection in the IR range at 800 nM in the presence of diastase.

Moreover, at a cell density range of 20,000 cells/well, the PAS stain IR fluorescence is glycogen specific, as diastase digestion of cellular glycogen mediates a time-dependent decrease in signal of about 2-fold (FIG. 2).

Conclusion

PAS IR fluorescence detection at 700 nm and 800 nm was demonstrated to be a viable method for easily quantitating relative glycogen levels in cells. In fibroblasts derived from a severe patient with Pompe disease, a glycogen storage disease, IR fluorescence was significantly greater than in normal fibroblasts. Also, the PAS signal was glycogen specific, as it was reduced after digestion with diastase. This approach can be extended to quantify absolute amounts of glycogen in cells and tissues by combining PAS staining of varying concentrations of an external glycogen standard, and quantifying the IR fluorescence emitted from these standard concentrations. A linear or non-linear regression analysis can be performed on the standard curve data, and the theoretical line or curve can be used to calculate absolute glycogen values from samples stained with PAS and measured using IR detection.

Example 2

Comparison of PAS with Detection in the Visible Range

As stated above, fluorescent microscopy, i.e., detection in the visible range, can be used to qualitatively detect glycogen following PAS staining. FIGS. 3A and 3B depict fluorescent imaging of control CRL-2076 and PM-12 cells, respectively. While this method can detect glycogen in samples, it is very tedious to quantitate absolute levels of glycogen. Moreover, it is less amenable for high-throughput applications, since automated 96-well or higher density microtiter plate fluorescence readers and scanners are usually not viable alternatives for visible range measurements due to low depth and spatial resolution that cannot overcome high background due to autofluorescence of biological materials in the visible range. As the number of samples increase, and the number of fluorophores that are imaged per sample increase, data acquisition and processing time is proportionally increased, and throughput is proportionally decreased.

Example 3

Diagnosis and Monitoring the Prognosis of Pompe Disease

As described above, Pompe disease is a rare disease affecting only about one in 40,000 individuals, and as a result, is under- and misdiagnosed. Compounding this, severity, age at onset, rate of disease progression, and extent of organ involvement can vary significantly from individual to individual. Conclusive diagnosis generally requires an enzyme assay test to demonstrate reduced or absent activity for the lysosomal enzyme acid α-glucosidase (GAA), using cultured skin fibroblasts, muscle biopsies, and lymphocytes.

Moreover, the only treatment for Pompe disease, enzyme replacement therapy with recombinant α-glucosidase (Myozyme), is only approved for infantile Pompe disease, and the approval was based on ventilator-free survival as the only clinical endpoint. The only secondary outcomes studied were unblinded assessments of motor function by the Alberta Infant Motor Scale (AIMS), which did not improve with treatment, and left-ventricular mass index, which improved with treatment. Thus, replacement enzyme is not effective at improving motor function, likely due to poor penetration and bioavailability to skeletal muscles. Surprisingly, glycogen reduction was not evaluated as a surrogate endpoint for enzyme replacement therapy.

An alternative therapy, which employs small molecules to "rescue" the deficient enzyme in Pompe patients who express some mutant α-glucosidase is currently in clinical trials. Small molecules are expected to have improved bioavailability and thus, more promising to improve motor function in this subset of patients.

Therefore, there remains need in the art for assays that can aid in the diagnosis of Pompe disease, and in monitoring the prognosis of individuals (and animal models) being treated for Pompe disease (such as by ERT or chaperone treatment). According to the method of the present invention, glycogen accumulation in tissues of infantile-onset Pompe patients can be monitored pre- and post-treatment, which may be a measure of efficacy or may ultimately provide a correlation with clinical outcome.

In conclusion, IR fluorescence has superior signal-to-noise, and signal penetration from thick tissues. It is also readily quantifiable and compatible with high-throughput applications. IR fluorescence detection is superior to optical density measurement and visible light fluorescence measurement for glycogen content quantification from stained cells or tissues.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A method for detecting polysaccharides in a biological sample, which method consists essentially of the sequential steps of
    subjecting the sample to Periodic Acid-Schiff staining to provide Periodic Acid-Schiff stained sample,
    washing the sample to remove unreacted Schiff's reagents followed by detecting light fluorescing from said Periodic Acid-Schiff stained sample at a wavelength in the range from about 700 nM to 800 nM;
    wherein the biological sample is isolated cells or tissue selected from the group consisting of liver, kidney, heart, brain and skeletal muscle.

2. The method of claim 1, wherein the polysaccharide is glycogen.

3. The method of claim 1, wherein the biological sample is derived from a human subject suspected of having a glycogen storage disease.

4. The method of claim 3, wherein the glycogen storage disease is selected from the group consisting of Pompe disease; Cori's-Forbes' disease; Andersen's disease; Tauri's disease; McArdle's disease; Phosphorylase b Kinase deficiency (Glycogenosis type VIII); equine Glycogen Branching Deficiency; Phosphoglycerate kinase A-isoform deficiency (Glycogenosis IX); Phosphoglycerate M-mutase deficiency (Glycogenosis type X); triosephosphate isomerase (TIM) deficiency; pulmonary interstitial glycogenosis; diabetic nephropathy; and Lafora's disease (myoclonus epilepsy).

5. The method of claim 4, wherein the glycogen storage disease is Pompe disease.

6. The method of claim 5, wherein the glycogen storage disease is infantile-onset Pompe disease.

7. The method of claim 1, which further comprises quantitating the level of polysaccharides present in the biological sample by comparing the amount of the light fluorescing from the periodic Acid-Schiff stained sample at a wavelength in the range from about 700 nM to 800 nM with that light fluorescing from standards of known quantities of polysaccharides.

8. A method for detecting glycogen in a biological sample from a subject having or suspected of having Pompe disease, which method consists essentially of the sequential steps of
    subjecting the sample to Periodic Acid-Schiff staining to provide Periodic Acid-Schiff stained sample,
    washing the sample to remove unreacted Schiff's reagents followed by detecting light fluorescing from said Periodic Acid-Schiff stained sample at a wavelength in the range from about 700 nM to 800 nM;
    wherein the biological sample is isolated cells or tissue selected from the group consisting of liver, kidney, heart, brain and skeletal muscle.

9. The method of claim 8, which further comprises quantitating the level of polysaccharides present in the biological sample by comparing the amount of the light fluorescing from the periodic Acid-Schiff stained sample at a wavelength in the range from about 700 nM to 800 nM with that light fluorescing from standards of known quantities of glycogen.

10. A method of monitoring the efficacy of treatment of a subject being treated for a glycogen storage disease, which method comprises
    i) detecting glycogen in a first biological sample derived from the subject prior to initiation of treatment according to the method of claim 1;
    ii) detecting glycogen in a second biological sample derived from the subject following initiation of treatment according to the method of claim 1;
    iii) quantitating the levels of glycogen in the two samples; and iv) comparing the level of glycogen in the first sample with the level of glycogen in the second sample;
wherein a reduction in the level of glycogen in the second sample indicates that the treatment is effective.

11. The method of claim 10, wherein the glycogen storage disease is Pompe disease.

* * * * *